United States Patent [19]

Kleinerman

[11] 4,036,946
[45] July 19, 1977

[54] IMMUNOFLUOROMETRIC METHOD FOR MEASURING MINUTE QUANTITIES OF ANTIGENS, ANTIBODIES AND OTHER SUBSTANCES

[76] Inventor: Marcos Kleinerman, South Point Road, Webster, Mass. 01550

[21] Appl. No.: 623,567

[22] Filed: Oct. 20, 1975

[51] Int. Cl.² .................... G01N 21/52; G01N 33/16
[52] U.S. Cl. ........................... 424/8; 23/230 B; 250/458; 424/12
[58] Field of Search .............. 23/230 B; 424/12, 8

[56] References Cited
U.S. PATENT DOCUMENTS 3,720,760   3/1973   Bennich ..................... 424/12 X Primary Examiner—Sidney Marantz
Attorney, Agent, or Firm—Morse, Altman, Oates & Bello

[57] ABSTRACT

A method and apparatus for measuring minute quantities of antigens, antibodies and other substances characterized by binding reactions with one another for forming a sandwich constituting an inner layer having a distribution of an unlabelled reagent, an intermediate layer having a distribution of the substance to be analyzed and an outer layer having a distribution of a fluorescent labelled reagent, the labelled and unlabelled reagents having the same biochemical specificity. Illumination from an excitation source is directed towards the sandwich and the fluorescence emitted by the fluorescent label is detected for measuring minute quantities of the substance under diagnosis.

11 Claims, 3 Drawing Figures

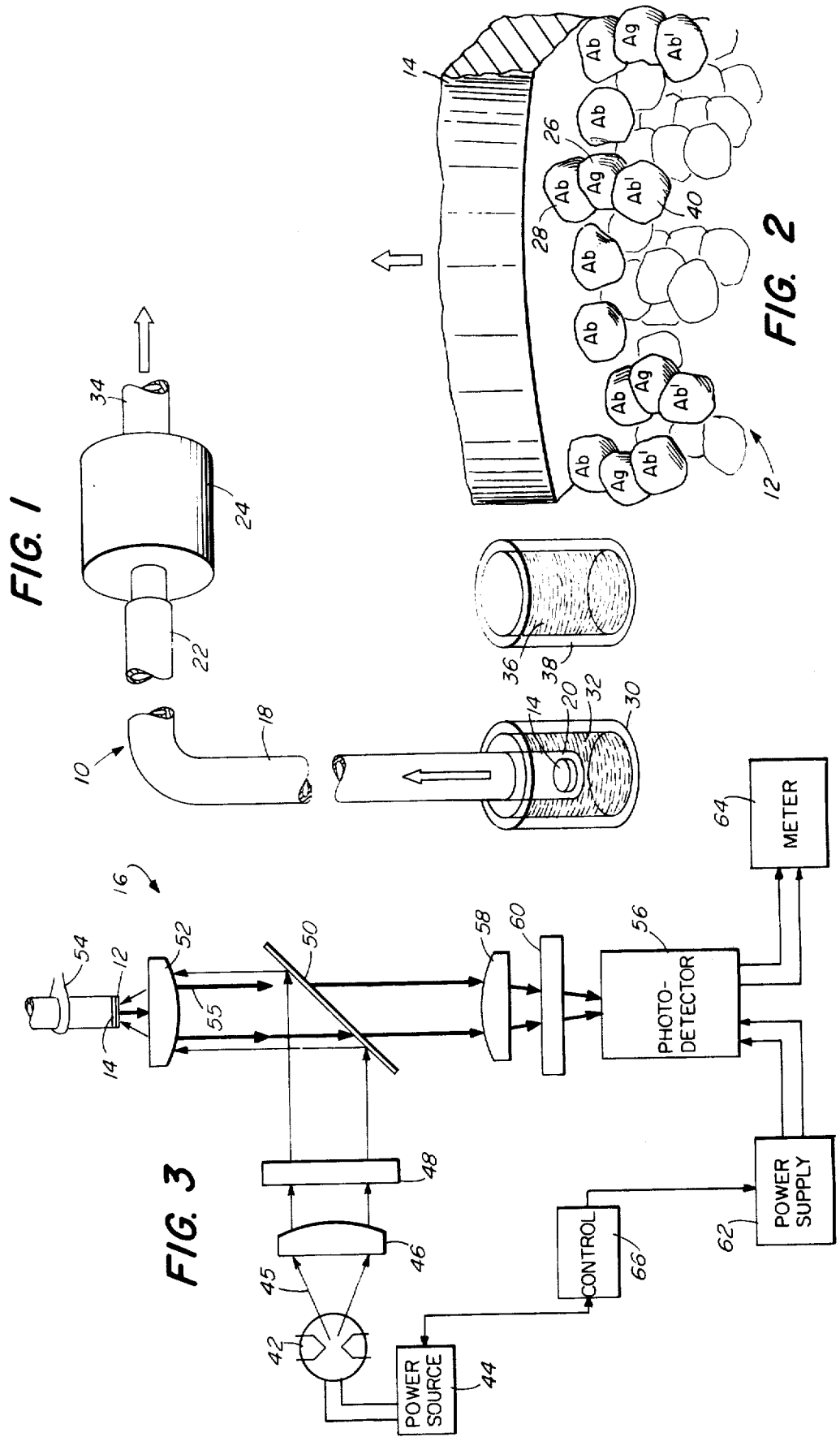

IMMUNOFLUOROMETRIC METHOD FOR MEASURING MINUTE QUANTITIES OF ANTIGENS, ANTIBODIES AND OTHER SUBSTANCES

BACKGROUND OF THE INVENTION

1. Field of Invention

The present invention relates to measuring methods and apparatuses and, more particularly, is directed towards methods and apparatuses for measuring minute quantities of antigens, antibodies and other substances.

2. Description of the Prior Art

In recent years, various methods and apparatuses have been designed for measuring minute quantities of antigens in biological samples. An antigen is an agent that stimulates the formation of a corresponding antibody and bindingly reacts therewith. An antibody is a member of a special class of serum proteins, referred to as immunoglobulins, which is formed as a response to an antigen and reacts specifically with it. Antibody-antigen reactions have a specificity comparable to that of enzymes. Generally, antibody or antigen assaying methods are based on these binding reactions which usually cause precipitation or agglutination. Often times, the precipitation or agglutination is visible to the naked eye. However, analysis of smaller concentrations require sensitive instrumentation.

At the cellular level, an antigen can be detected by treatment with a solution of its specific antibody molecules which are labelled with a fluorescent tracer. After washing off excess labelled antibody molecules, the sample (usually in a microscope slide) is illuminated with light absorbed by the fluorescent tracer. The cells containing the antigen will show the characteristic fluorescence of the tracer.

In cell-free serum, one has to separate the formed antigen-antibody complex from the rest of the serum and the excess reagents, and then measure the concentration of the labelling agent, which should be proportional to the original concentration of the antigen (or antibody). Very often a clinically significant concentration is so small that radioactive tracer methods are employed. The most used radioactive tracer is Iodine 125 ($I^{125}$), a gamma emitting isotope of Iodine.

One method for detecting hepatitis associated antigen (HAA) uses a polystyrene tube that has a coating of an unlabelled specific antibody molecules on its inner walls. Next, a serum containing the HAA is incubated in the tube for several hours. Next, the tube is washed. The HAA particles are trapped by the unlabelled antibody molecules. Next, the tube is incubated with a solution containing the specific antibody molecules with Iodine 125 attached thereto. The radioactive specific antibody molecules attach to the HAA particles and form a structure in which the HAA particles are sandwiched between an unlabelled molecule and a labelled radioactive molecule. Then, the tube is washed to remove excess labelled molecules. Finally, the tube is placed within a radioactivity counter for determining the HAA content of the test serum, the number of gamma counts being proportional to the number of HAA particles contained in the test serum sample. In U.S. Pat. No. 3,896,218, S. E. Charm discloses a method of determining the hepatitis associated antigen content of blood using immobilized HAA particles and a radioactive labelled antibody.

Present methods and apparatuses for measuring minute quantities of antigens, antibodies and other substances suffer from the disadvantages that the instrumentation required is relatively complex, the time consumed for such measurements is lengthly, and some radioactive labelled compounds decay too quickly. A need has arisen for methods and apparatuses which can rapidly and accurately measure minute quantities of antigens, antibodies and other substances using relatively simple instrumentation.

SUMMARY OF THE INVENTION

It is an object of the present invention to provide methods and apparatuses for rapidly and accurately measuring minute quantities of antigens, antibodies and other substances using relatively simple instrumentation.

It is another object of the present invention to provide methods and apparatuses for rapidly and accurately measuring minute quantities of antigens, antibodies and other substances by forming a layered structure on a base stratum. The layer structure includes an inner stratum of a unlabelled substance that is attached to the base stratum, an intermediate stratum of a substance to be measured that is attached to the inner stratum, and an outer stratum of a fluorescent labelled substance that is attached to the intermediate stratum. The unlabelled substance and the fluorescent labelled substance are characterized by a similar binding reaction with the substance to be measured. The layered structure is illuminated by an excitation source and the flourescence emitted by the labelled substance is detected and measured to provide an indication of the quantity of the substance to be measured.

Other objects of the present invention will in part be obvious and will in part appear hereinafter.

The invention accordingly comprises the devices, together with their parts, elements and interrelationships, that are exemplified in the following disclosure, the scope of which will be indicated in the appended claims.

BRIEF DESCRIPTION OF THE DRAWINGS

A fuller understanding of the nature and objects of the present invention will become apparent upon consideration of the following detailed description taken in connection with the accompanying drawings, wherein:

FIG. 1 is a perspective view of an apparatus for forming a layered structure on a base stratum in accordance with the present invention;

FIG. 2 is a schematic diagram illustrating certain principles of the invention; and FIG. 3 is a schematic diagram of a system embodying the invention for measuring minute quantities of a substance contained in the layered structure of FIG. 1.

DETAILED DESCRIPTION OF THE PREFERRED EMBODIMENTS

FIG. 1 shows an apparatus 10 for forming a layered structure of the type generally shown in FIG. 2 at 12 on a base stratum 14 and FIG. 3 shows a system 16 for measuring minute quantities of a substance that is part of the layered structure. The substances forming layered structure 12, which is comprised of regular and/or irregular distributions of the substances, are characterized by binding reactions. In particular, layered structure 12 includes distributions of substances such as antigens and antibodies. An antigen is an agent that stimulates the formation of a corresponding antibody, the formed antibody reacting with the antigen. An antibody is a member of a select class of serum proteins, referred to as immunoglobulins, which is formed as a result of an antigen and reacts with that specific antigen. In one example, an antibody is used to determine the presence and concentration of its specific antigen. In another example, an antigen is used to determine the presence and concentration of its specific antibody.

Apparatus 10 comprises a tubular member 18 having open ends 20 and 22. Base stratum 14, for example a porous disc containing a polymeric matrix is snugly received within end 20 coaxial with tubular member 18. Preferably, the diameter of disc 14 is in the range of 0.1 to 10.0 mm and specifically is in the range of 0.5 to 5.0 mm. The thickness of disc 14 preferably is in the range of 0.05 to 2.0 mm and specifically is in the range of 0.1 to 0.5 mm. In the illustrated embodiment, the diameter and thickness of disc 14 is 2.0 and 0.2 mm, respectively. The inside diameter of tubular member 18, for example a glass tube, is such as to snugly receive disc 14. A suction device 24 is connected to end 22 of tube 18.

The method for forming layered structure 12 comprises the steps of first preparing a base stratum 14 having an unlabelled reagent that bindingly reacts with a substance to be analyzed, the presence and concentration of which is to be detected and measured. Next, inserting base stratum 14 into tubular member 18. Next, immersing tubular member 18 and base stratum 14 into a first solution containing the substance to be analyzed. Next, forming an intermediate layer having a distribution of the substance to be analyzed by making the first solution flow through the base stratum, the substance to be analyzed attaching to a distribution of the unlabelled reagent which constitutes an inner layer. Next, preparing a second solution containing a labelled reagent that bindingly reacts with the substance to be analyzed, the labelled reagent having a fluorescent label. Then, immersing tubular member 18 and base stratum 14 into the second solution. Finally, forming layered structure 12 by making the second solution flow through the intermediate layer, the third substance attaching to the substance to be analyzed and forming a final layer having a distribution of the labelled reagent. The number of molecules of the labelled reagent attached to the substance to be analyzed is determined by the number of molecules of the substance to be analyzed that is attached to the unlabelled reagent. The number of labelled molecules corresponds to the number of molecules in the substance to be analyzed.

In one example, the substance to be analyzed and measured is an antigen 26, the antigen particles are denoted as A$g$ in FIG. 2. Disc 14 is composed of a porous polymeric material such as porous glass coated with agarose gel in such a way that disc 14 remains porous to liquid flow. The diameter of disc 14 is 2.0 mm in order to (a) maximize the antigen concentration and, hence, that of the fluorescence tag, (b) achieve good collection efficiency of the fluorescence, and (c) minimize background fluorescence at the lower concentrations of antigen. The unlabelled reagent is an antibody 28, which reacts specifically with the antigen to be detected and measured, is attached covalently or by physical absorption, for example, to disc 14. The antibody particles are denoted as A$b$ in FIG. 2. Tube 18 is placed within a receptacle 30 containing a solution 32 in which antigens 26 may be present. Suction device 24 is energized and solution solution 32 flows from receptacle 30 through disc 14 and tube 18 and exits a discharge port 34. Antigen particles 26 in solution 32 are trapped by the immobilized antibody particles on disc 14. Next, tube 18 is placed into a solution 36 containing the labelled reagent. Solution 36, which is contained in a receptacle 38, includes antibody molecules 28 that have a fluorescent label attached thereto, the labelled antibody molecules denoted by reference character 40 and A$b'$ in FIG. 2. Suction device 24 draws solution 36 from receptable 38 and passes it through disc 14. Labelled antibody molecules 40 attach themselves to the trapped antigen particles 26, thus forming layered structure 12. That is, apparatus 10 forms a layered structure comprising a first or inner layer having a distribution of unlabelled antibody molecules 28 that are immobilized on disc 14, an intermediate layer having a distribution of antigen particles 26 that are trapped by the immobilized antibody molecules, and a third or outer layer having a distribution of labelled antibody molecules that are attached to the trapped antigens. Disc 14 is washed to remove excess antibody molecules. System 16 is utilized for measuring the antigen concentration of layered structure 12.

In one method for preparing a labelled antibody, a fluorescent molecule such as fluoroscein is attached to an antibody molecule (a gamma-globulin) by reacting its isothiocynate derivative (fluorescein isothiocynate) with available amino ($NH_2$) groups in the gamma-globulin. The reaction product is an antibody molecule having a fluorescein molecule attached to it. The antibody thus labelled with the fluorescein molecule maintains its antibody specificity and is rendered fluorescent by exciting it with light that the fluorescein molecule absorbs. In an alternative embodiment, a fluorescent molecule other than fluorescein is attached to the antibody, for example, a fluorescent molecule such as N,N,N',N' - Tetramethyl rhodamine is incorporated into an antibody molecule through its isothiocyanate derivative. The N,N,N',N' - tetramethyl rhodamine molecule is excited in the green region and emits in the red region. Fluorescein is excited in the blue region and emits in the green region. In the illustrated embodiment of system 16, in FIG. 3, antibody molecules 40 are labelled with N,N,N',N' - tetramethyl rhodamine.

Referring now to FIG. 3, it will be seen that system 16 comprises an excitation source 42 which is connected to a power supply 44. Excitation source 42, for example a mercury arc lamp, generates a light beam 45 that is directed through a planoconvex lens 46 and a filter 48 towards a dichroic mirror 50. In the illustrated embodiment, by way of example, filter 48 is a mercury line filter that passes green light in the 546 nanometer mercury band. Dichroic mirror 50 is highly reflective to green light and is highly transmissive to red light. The light beam reflected by dichroic mirror 50 passes through a planoconvex lens 52 and is directed towards layered structure 12, tubular member 18 being captively held by a fastener 54, for example a clamp. Labelled antibodies 40 are excited by the light directed thereto and emit red light 55 which is transmitted through dichroic mirror 50. The transmitted light is directed towards a photodetector 56 via a planoconvex lens 58 and a filter 60 which passes only red light, for example. Photodetector 56, for example a photomultiplier tube which is powered by a high voltage supply 62, is coupled to a measuring device 64. Photomultiplier tube 56 generates a current that is proportional to the intensity of the light emitted by labelled antibody molecules 40.

Measuring device 64, for example a dc ammeter or a photon counter measures the output signal generated by photomultiplier tube 56 and presents an indication of the presence and concentration of the labelled antibody molecules 40 which is directly related related to the number of antigen molecules 26 in layered structure 12. The thickness of disk 14 is such that the labelled reagent is in the field-of-view of photodetector 56.

The fluorescent signal S generated by system 16, expressed in photoelectrons per second at the photocathode surface (before electron multiplication) is:

$$S = P(\lambda/hc) \cdot \alpha \cdot [\epsilon N] \cdot \phi \cdot \beta \cdot q \cdot t$$

where:
- $P$ is the power radiated by light source 42 in all directions, within the effective excitation band of the fluorescent label.
- $\lambda$ is the excitation wavelength
- $h$ is Planck's constant
- $c$ is the velocity of light
- $\alpha$ is the fraction of P incident in the flourescent antibody molecules
- $\epsilon$ is the absorbtion coefficient per labelled antibody molecule
- $N$ is the number of labelled antibody molecules per square centimeter of the illuminated field
- $\phi$ is the fluorescence quantum efficiency
- $\beta$ is the fraction of the emitted fluorescence which reaches the photocathode of photomultiplier tube 56
- $q$ is the photoelectric quantum efficiency of the photocathode
- $t$ is the collection time of the fluorescence, not longer than the time constant of the measuring device In the following example, the fluorescent label is efficiently excited by the 546 nanometer mercury band. A short arc (0.3 mm), high pressure, 100 watt mercury arc is used to excite the labelled antibodies and 200 milliwatts of the 546 mm band reach disk 14. The fluorescent signal is $2.1 \times 10^3$ photoelectrons per second when $\epsilon = 2.5 \ 10^{-17}$ per molecule
$N = 10^4$ molecules
$\phi = 0.5$
$\beta = 0.3$
$q = 0.1$
$t = 1$ second The signal-to-noise ration is increased further by operating arc lamp 42 in a pulsed mode and gating photomultiplier tube 56 for the duration of the pulse by means of a controller 66. This eliminates most of the photomultiplier dark noise. The main factor limiting sensitivity is the residual fluorescence of the agarose gel which is minimized by utilizing a fluorescent tag in the red or near IR having a narrow emission band.

Since certain changes may be made in the foregoing disclosure without departing from the scope of the invention herein involved, it is intended that all matter contained in the above description and depicted in the accompanying drawings be construed in an illustrative and not in a limiting sense.

What is claimed is:
1. A method for measuring minute quantities of a substance comprising the steps of:
   a. immobilizing molecules of an unlabelled reagent on a porous base stratum, said unlabelled reagent having a binding reaction with said substance to be measured;
   b. immersing said base stratum into a solution containing said substance to be measured;
   c. making said solution containing said substance to be measured flow through said immobilized molecules and said porous base stratum;
   d. forming an intermediate layer having a distribution of said substance to be measured on said immobilized unlabelled reagent as said solution containing said substance to be measured flows through said immobilized molecules, particles of said substance to be measured being trapped by said immobilized molecules of said unlabelled reagent;
   e. immersing said base stratum with said intermediate layer into a solution containing a labelled reagent;
   f. making said solution containing said labelled solution flow through said intermediate layer and said base stratum;
   g. forming a layer having a distribution of said labelled reagent on said intermediate layer, said labelled reagent being essentially said unlabelled reagent with a fluorescent label, molecules of said labelled reagent having a fluorescent label attaching to said trapped particles of said substance to be measured as said solution containing said labelled reagent flows through said intermediate layer; and
   h. measuring said molecules of said labelled reagent for determining the concentration of said substance to be measured.

2. The method as claimed in claim 1 wherein said unlabelled reagent is an antibody.

3. The method as claimed in claim 2 wherein said substance to be measured is an antigen, said antibody being specific to said antigen.

4. The method as claimed in claim 3 wherein said labelled reagent is said specific antibody having a fluorescent label.

5. The method as claimed in claim 1 wherein said measuring step includes the steps of:
   a. generating a light beam for exciting said fluorescent labelled reagent; and
   b. detecting light emitted by said excited fluorescent labelled reagent.

6. The method as claimed in claim 1 wherein said base stratum is a disc having a diameter in the range of 0.1 to 10 mm.

7. The method as claimed in claim 6 wherein said disc has a diameter of approximately 2 mm and a thickness in the approximate range of 0.1 to 0.5 mm.

8. A method for measuring minute quantities of a substance comprising the steps of:
   a. immobilizing molecules of an unlabelled reagent on a porous base stratum received within a tubular member, said unlabelled reagent having a binding reaction with said substance to be measured;
   b. making a solution containing said substance to be measured flow through said immobilized molecules of said unlabelled reagent and said base stratum to form an intermediate layer having a distribution of said substance to be measured, particles of said substance to be measured being trapped by said unlabelled reagent, said intermediate layer of said trapped particles formed on said immobilized molecules of said unlabelled reagent;
   c. making a solution containing a labelled reagent having a fluorescent label flow through said intermediate layer and said base stratum, molecules of said labelled reagent attaching to said trapped particles of said substance to be measured and forming an outer layer having a distribution of said labelled reagent; and d. determining the concentration of said substance to be measured by exciting said fluorescent labelled molecules of said outer layer with an excitation source and detecting light emitted by said excited molecules.

9. The method as claimed in claim 8 wherein said base stratum is a disc having a diameter in the range of 0.5 to 5.0 mm.

10. The method as claimed in claim 8 wherein said porous base stratum is a porous disc having a polymeric matrix to which said unlabelled reagent is attached.

11. The method as claimed in claim 10 wherein said polymeric matrix is agarose, said substance to be measured is an antigen, said unlabelled reagent is an antibody specific to said antigen, and said labelled reagent is said specific antibody having a fluorescent label.

* * * * *